(12) United States Patent
Cho

(10) Patent No.: US 10,426,901 B2
(45) Date of Patent: Oct. 1, 2019

(54) SYRINGE CAP HAVING REUSE PREVENTION STRUCTURE

(71) Applicant: Hee Min Cho, Gunsan (KR)

(72) Inventor: Hee Min Cho, Gunsan (KR)

( * ) Notice: Subject to any disclaimer, the term of this patent is extended or adjusted under 35 U.S.C. 154(b) by 233 days.

(21) Appl. No.: 15/666,366

(22) Filed: Aug. 1, 2017

(65) Prior Publication Data

US 2018/0296774 A1    Oct. 18, 2018

(30) Foreign Application Priority Data

Apr. 12, 2017   (KR) ........................ 10-2017-0047575

(51) Int. Cl.
*A61M 5/00* (2006.01)
*A61M 5/50* (2006.01)
*A61M 39/20* (2006.01)
*A61M 5/32* (2006.01)
*A61M 5/31* (2006.01)

(52) U.S. Cl.
CPC ........ *A61M 5/5086* (2013.01); *A61M 5/3134* (2013.01); *A61M 5/3204* (2013.01); *A61M 5/50* (2013.01); *A61M 39/20* (2013.01); *A61M 2005/312* (2013.01); *A61M 2005/3104* (2013.01); *A61M 2205/273* (2013.01)

(58) Field of Classification Search
CPC ............ A61M 5/31; A61M 2005/3103; A61M 2005/3117; A61M 2005/3118; A61M 2205/27; A61M 2205/276; A61M 5/3202; A61M 5/3205; A61M 5/321; A61M 5/3213; A61M 2005/3104; A61M 2005/312; A61M 2205/273; A61M 39/20; A61M 5/3134; A61M 5/3204; A61M 5/50; A61M 5/5086

USPC ......................................................... 604/111
See application file for complete search history.

(56) References Cited

U.S. PATENT DOCUMENTS

| | | | | |
|---|---|---|---|---|
| 5,135,496 A | * | 8/1992 | Vetter ..................... | A61M 5/34 604/111 |
| 7,374,555 B2 | * | 5/2008 | Heinz ................. | A61M 5/5086 604/111 |
| 10,099,012 B2 | * | 10/2018 | Haefele ............... | A61M 5/3134 |

FOREIGN PATENT DOCUMENTS

| | | |
|---|---|---|
| JP | 2009-526581 A | 7/2009 |
| JP | 2010-233838 A | 10/2010 |
| KR | 10-2010-0138905 A | 12/2010 |
| KR | 10-1027861 B1 | 4/2011 |
| KR | 10-2013-0017766 A | 2/2013 |

(Continued)

*Primary Examiner* — Jason E Flick
(74) *Attorney, Agent, or Firm* — KORUS Patent, LLC; Seong Il Jeong

(57) ABSTRACT

Disclosed is a syringe cap having a reuse prevention structure, including a reuse prevention cover which fixes a fixed body to the front end of a syringe barrel by fusion or welding, combines a separable body with the fixed body by a screw, and entirely covers the separable body and the fixed body, wherein the reuse prevention cover includes an upper body and a lower body. The upper body and the lower body are connected to each other by a connection breakable portion, and the connection breakable portion is broken by rotating the upper body in one direction relative to the lower body such that the upper body and the separable body are separated from the lower body and the fixed body, respectively. In addition, the connection breakable portion is easily broken by the twisting of the reuse prevention cover, and by the pushing-up motion of the separable body.

5 Claims, 10 Drawing Sheets

(56) References Cited

FOREIGN PATENT DOCUMENTS

KR 10-1361088 B1 2/2014

\* cited by examiner

SYRINGE CAP HAVING REUSE PREVENTION STRUCTURE

CROSS REFERENCE TO RELATED APPLICATION

The present application claims priority to Korean Patent Application No. 10-2017-0047575, filed Apr. 12, 2017, the entire contents of which is incorporated herein for all purposes by this reference.

BACKGROUND OF THE INVENTION

Field of the Invention

The present invention relates to a syringe cap covering a dispensing tip provided at a front end of a syringe and having a reuse prevention structure. More particularly, the present invention relates to a syringe cap having a reuse prevention structure, the cap including a reuse prevention cover fitted over a fixed body and a separable body of the syringe cap, wherein the reuse prevention cover includes an upper body and a lower body integrally connected to each other by a connection breakable portion such that the connection breakable portion is broken by both a rotary motion of the upper body relative to the lower body and the pushing-up motion of the separable body from the fixed body so as to separate both the upper body and the separable body covered with the upper body from the fixed body, thereby preventing the reuse of the syringe cap.

Description of the Related Art

Generally, a syringe is a medical supply, used for various purposes, such as injecting a medicinal fluid and collecting blood or samples.

A syringe is composed of a syringe barrel, a piston inserted into the syringe barrel, and a piston rod operating the piston by applying pressure. In addition, according to the purpose of use, the syringe is used by coupling an injection needle, a syringe cap, or a blood collecting tool to an upper dispensing tip of the syringe barrel.

After used once, such a syringe must be discarded to prevent reuse because a blood residue of a patient remains on an injection needle of a used syringe. If the used syringe containing a blood residue is used again, pathogens included in the blood residue remaining on the injection needle are directly transferred to other persons. Accordingly, a secondary infection accident occurs by the transferred pathogens.

For this reason, a syringe used once is discarded to prevent reuse. In some cases, however, used syringes are frequently reused without destruction thereof to reduce purchase costs of syringes, thereby causing both infection caused by transfer of diseases and a social problem caused by the infection.

Recently, a disposable syringe has been used to prevent reuse of a syringe. Also, it can be checked whether a disposable syringe has been used by improving the syringe structure, thereby preventing reuse of the syringe.

However, the structure of a conventional disposable syringe cannot be applied to a general syringe, so a disposable syringe must be manufactured separately from a general syringe.

In the techniques proposed to solve problems caused by reusing a conventional syringe, Patent Document 1 discloses a syringe cap for preventing reuse, which is opened by cutting a cutting part of a cap body. In this patent, luer lock with a screw coupling portion on an inner circumference is integrally formed on an outer surface of a dispensing tip for discharging contents on a front end of a syringe barrel, and the syringe cap is tightly combined with the luer lock. Here, the syringe cap includes a rubber packing for tightly blocking a dispensing tip inside a cylindrical cap body and a closing cap locking the rubber packing at the back of the rubber packing. The syringe cap is elastically fitted over the luer lock such that latching projections formed on a plurality of positions on a front inner circumference of the cap body are engaged with latching grooves formed on an upper part of the outer circumferential surface of the luer lock. In the cylindrical cap body, an upper body and a lower body are integrally connected to each other by breakable portions famed around a circumference of a junction between the upper body and the lower body at regular intervals, and the breakable portions are broken to open the syringe cap.

According to the conventional technique, when a syringe is used, the syringe cap is opened by breaking the breakable portions by twisting the upper body from the lower body upward and downward. Accordingly, it can be checked whether the syringe has been used by checking the breakage of the breakable portions, thus reuse of the syringe may be prevented.

However, the conventional technique provides a structure where the lower body and the upper body are integrally connected by the breakable portions, and the rubber packing is combined therein, thus it can only be applied to a structure where a luer lock is integrally formed on a front end of a syringe barrel. Thus, the use of the conventional technique is limited. Furthermore, since the breakable portions of the upper body and the lower body are broken by twisting the upper body upward and downward, the breaking motion is not easy. Moreover, in the case of a new user, it is inconvenient to use the syringe cap because the method of breaking the syringe cap is difficult to perform.

In addition, since the breakable portions are broken by twisting the upper body upward and downward, debris, such as sharp burrs, are formed on the top of the lower body. Accordingly, when the syringe is used, safety accidents, such as hands injuries, may occur.

DOCUMENT OF RELATED ART (Patent Document 1) Korean Patent Application Publication No. 10-2013-0017766

(Patent Document 2) Korean Patent Application Publication No. 10-2010-0138905

(Patent Document 3) Korean Patent No. 10-1027861

SUMMARY OF THE INVENTION

Accordingly, the present invention has been made keeping in mind the above problems occurring in the related art, and an object of the present invention is to provide a syringe cap having a reuse prevention structure, including a reuse prevention cover which fixes a fixed body to the front end of a syringe by fusion or welding, combines a separable body with the fixed body by a screw, and entirely covers the separable body and the fixed body, wherein the reuse prevention cover includes: an upper body fitted over an outer surface of the separable body; and a lower body fitted over an outer surface of the fixed body. The upper body and the lower body are connected to each other by a connection breakable portion, and the connection breakable portion can be broken by both an external force caused by rotation generated when rotating the upper body in one direction relative to the lower body, and the pushing-up motion of the separable body relative to the fixed body such that the upper body and the separable body are separated from the lower body and the fixed body, respectively. Furthermore, since it can be checked whether a syringe is usable by checking whether the connection breakable portion is broken, reuse of the syringe may be prevented. Moreover, since the fixed body is stably fixed to a syringe barrel, the upper body of the reuse prevention cover can easily be separated from the lower body thereof, and safety accidents caused by the connection breakable portion can be prevented.

In order to achieve the above object, the present invention provides a syringe cap having a reuse prevention structure, the syringe cap including: a fixed body with a spiral protrusion on an inner circumferential surface thereof, into which a dispensing tip of a syringe barrel is fitted, and whose bottom is coupled to the syringe barrel by a fusion welding portion; a separable body with a spiral groove on a lower part of an outer circumferential surface thereof, the spiral groove being spirally engaged with the spiral protrusion provided on the inner circumferential surface of the fixed body; a rubber packing fitted in the separable body to seal and block the dispensing tip of the syringe barrel coupled to the fixed body; and a reuse prevention cover fitted over the fixed body and the separable body to cover the fixed body and the separable body, wherein the reuse prevention cover includes: an upper body fitted over the separable body to cover an outer surface of the separable body; a lower body fitted over the fixed body to cover an outer surface of the fixed body, and positioned below a lower end of the upper body such that a top of the lower body is spaced apart from a bottom of the upper body; and a connection breakable portion which integrally connects the upper body and the lower body by connecting the bottom of the upper body to the top of the lower body, and is broken by rotating the upper body relative to the lower body in a direction to separate the bottom of the upper body from the top of the lower body, such that the separable body covered with the upper body is separated from the fixed body to open the fixed body, and wherein the spiral protrusion of the fixed body includes a tapered first pushing slope, and the spiral groove of the separable body includes a second pushing slope corresponding to the first pushing slope such that when rotating the upper body of the reuse prevention cover in one direction relative to the lower body in a state of pushing the upper body toward the lower body, the upper body is pushed up by the lower body, thereby being easily broken due to breaking of the connection breakable portion connecting the upper body and the lower body to each other.

In the syringe cap, the connection breakable portion of the reuse prevention cover, which connects the bottom of the upper body to the top of the lower body, may be in a tapered shape that gradually narrows from the bottom of the upper body to the top of the lower body, and wherein the bottom of the upper body, on which the connection breakable portion is provided, may further include a concave portion which is connected to the connection breakable portion and is concaved upward from the bottom of the upper body such that the bottom of the connection breakable portion is easily broken from the top of the lower body by twist of the connection breakable portion when rotating the upper body in one direction relative to the lower body.

Furthermore, in the syringe cap, on an upper part of the outer circumferential surface of the upper body of the reuse prevention cover, the upper body may further include an inclined portion inclined downward from the upper part of the outer circumferential surface of the upper body to be easily inserted into a syringe tray insertion hole.

Furthermore, in the syringe cap, on the inner circumferential surface of the lower body, which is fitted over the outer surface of the fixed body, of the reuse prevention cover, the lower body may further include: a plurality of slip prevention protrusions configured to come into close contact with the outer circumferential surface of the fixed body to prevent a slip of the lower body when rotating the upper body relative to the lower body; and a joint portion which is provided between the plurality of slip prevention protrusions by using one of an adhesive, high frequency fusion, and thermal fusion to firmly join the lower body to the fixed body.

Furthermore, in the syringe cap, the lower body may further include a plurality of radially-spaced cut portions configured to be opened when the upper body and the lower body are fitted over the separable body and the fixed body, and to be closed again when the lower body is completely fitted over the fixed body, thereby allowing the upper body and the lower body of the reuse prevention cover, which are connected to each other by the connection breakable portion, to be easily fitted over the outer surfaces of the separable body and the fixed body.

According to the present invention, the upper body and the lower body of the reuse prevention cover are fitted to entirely cover the fixed body and the separable body in a state of being integrally combined by the connection breakable portion, and the upper body and the lower body are tightly attached to the outer surfaces of the separable body and the fixed body, respectively. Accordingly, the connection breakable portion is broken by both the external force caused by rotation generated when rotating the upper body of the reuse prevention cover in one direction relative to the lower body thereof, and the pushing-up motion of the separable body from the fixed body such that the separable body is separated from the fixed body. Thus, reuse of the syringe may be prevented because it can be checked whether the syringe has been used by checking the whether the connection breakable portion is broken.

In addition, when rotating the upper body of the reuse prevention cover in one direction relative to the lower body thereof, since the fixed body whose outer surface is tightly attached to and is covered with the upper body is stably fixed to the front end of the syringe barrel by fusion or welding, the rotation of the lower body can be prevented. Thus, the separable body can easily be separated from the fixed body by rotating the upper body.

In addition, when separating the separable body of the reuse prevention cover from the fixed body thereof, as the separable body is pushed up from the fixed body by a tapered pushing slope, the connection breakable portion is easily broken. Also, the connection breakable portion is in a tapered shape that gradually narrows toward the lower body, so the connection breakable portion may be easily broken, thereby preventing the generation of burrs.

In addition, since the lower body of the reuse prevention cover is stably attached to the fixed body fixed and coupled to the front end of the syringe barrel by the slip prevention protrusions, a slip between the lower body and the fixed body may be prevented when rotating the upper body in a state of holding the lower body with a hand.

In addition, since the reuse prevention cover including the upper body and the lower body are easily fitted over and combined with the separable body and the fixed body, assembling efficiency and work efficiency are greatly improved.

DETAILED DESCRIPTION OF THE INVENTION

Figure 1:
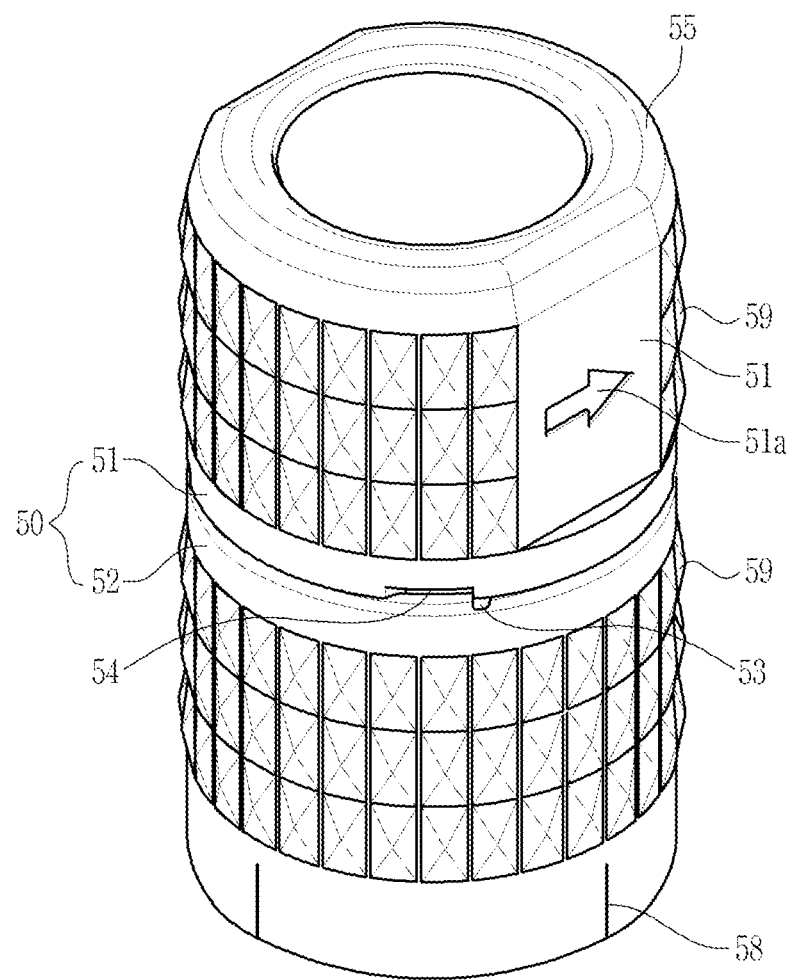
FIG. 1 is a perspective view illustrating a syringe cap having a reuse prevention structure.
Figure 2:
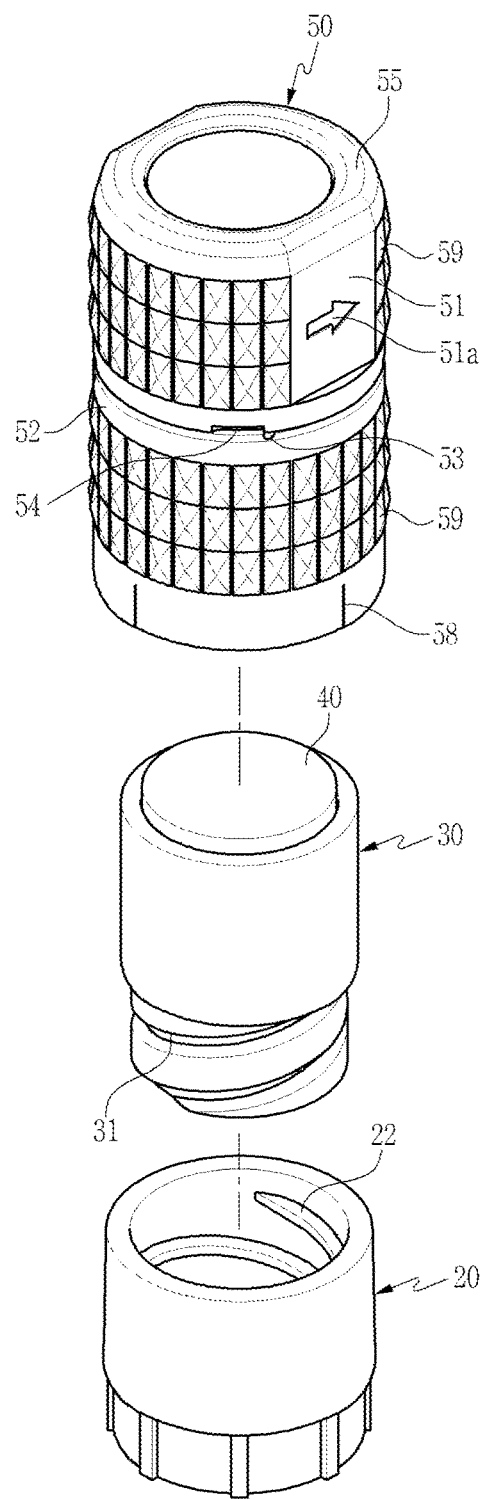
FIG. 2 is an exploded perspective view illustrating the construction of the syringe cap having a reuse prevention structure.
Figure 3:
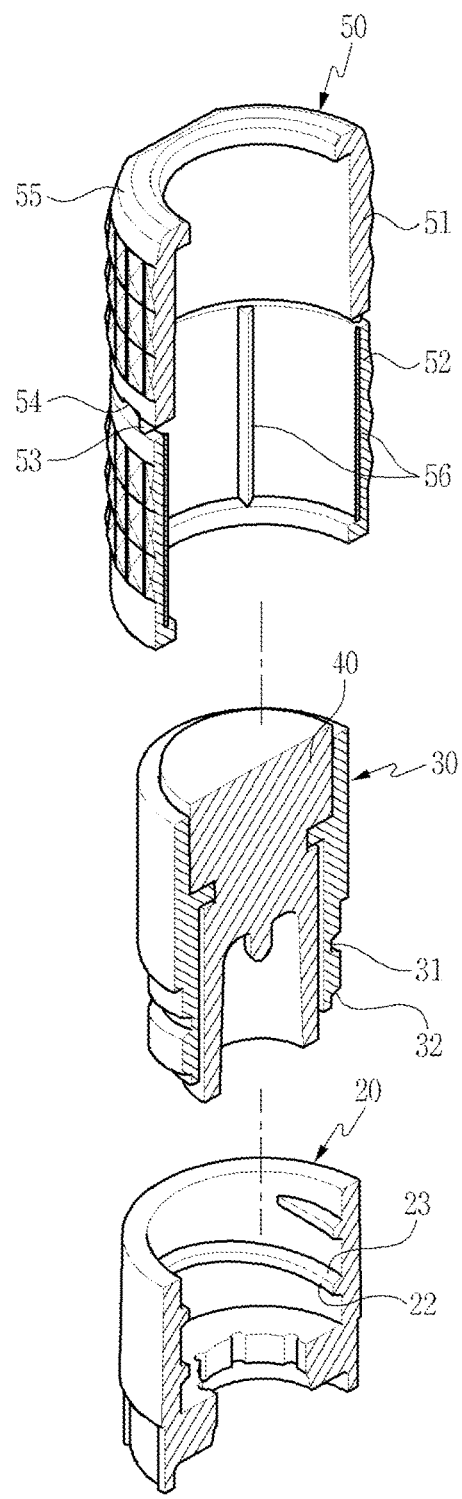
FIG. 3 is a partially sectioned exploded perspective view illustrating the construction of the syringe cap having a reuse prevention structure.
Figure 4:
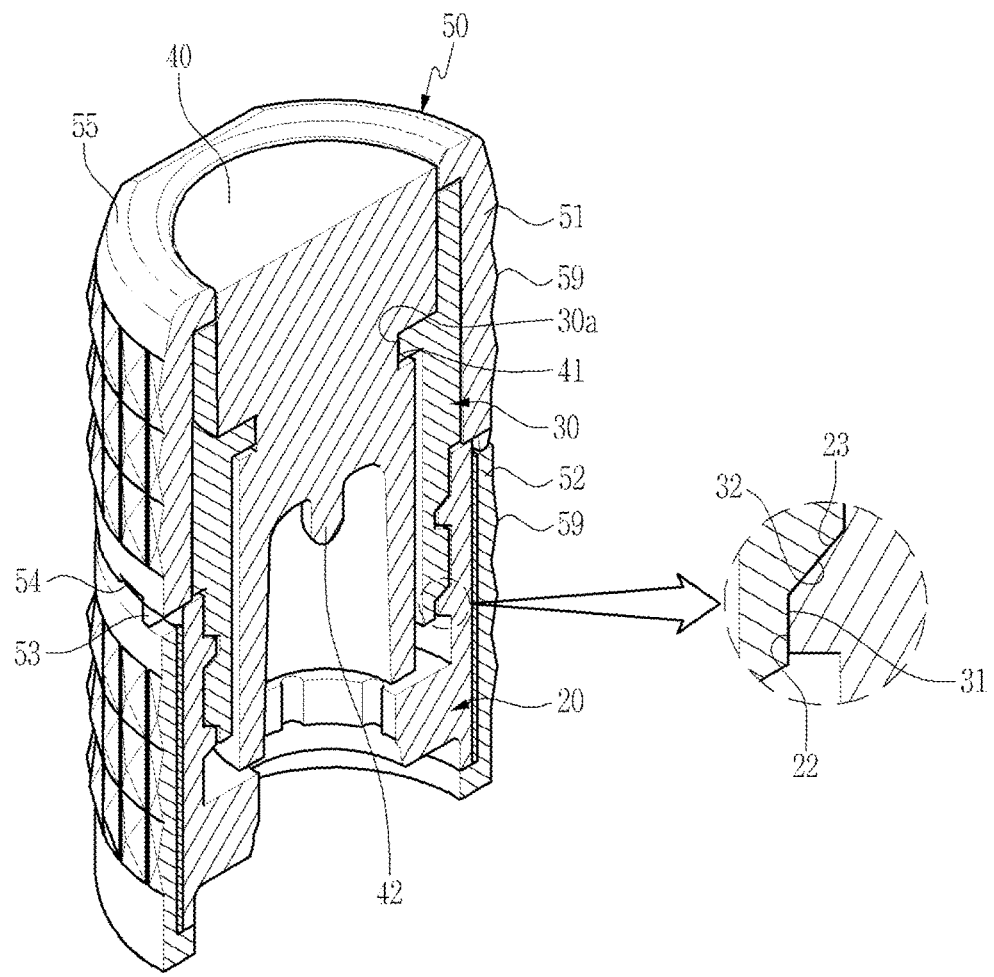
FIG. 4 is a partially sectioned perspective view illustrating the construction of the syringe cap having a reuse prevention structure.
Figure 5:
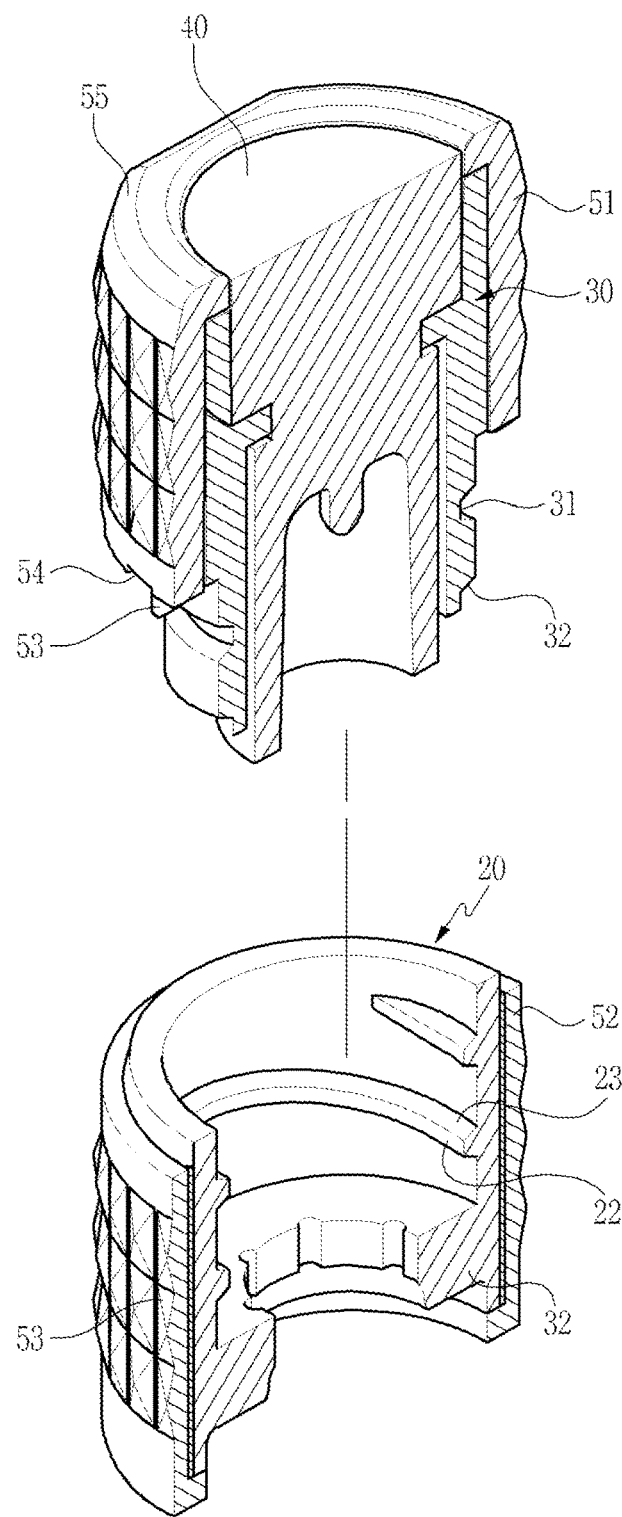
FIG. 5 is a partially sectioned exploded perspective view illustrating a separated state of a reuse prevention cover of the syringe cap having a reuse prevention structure.
Figure 6:
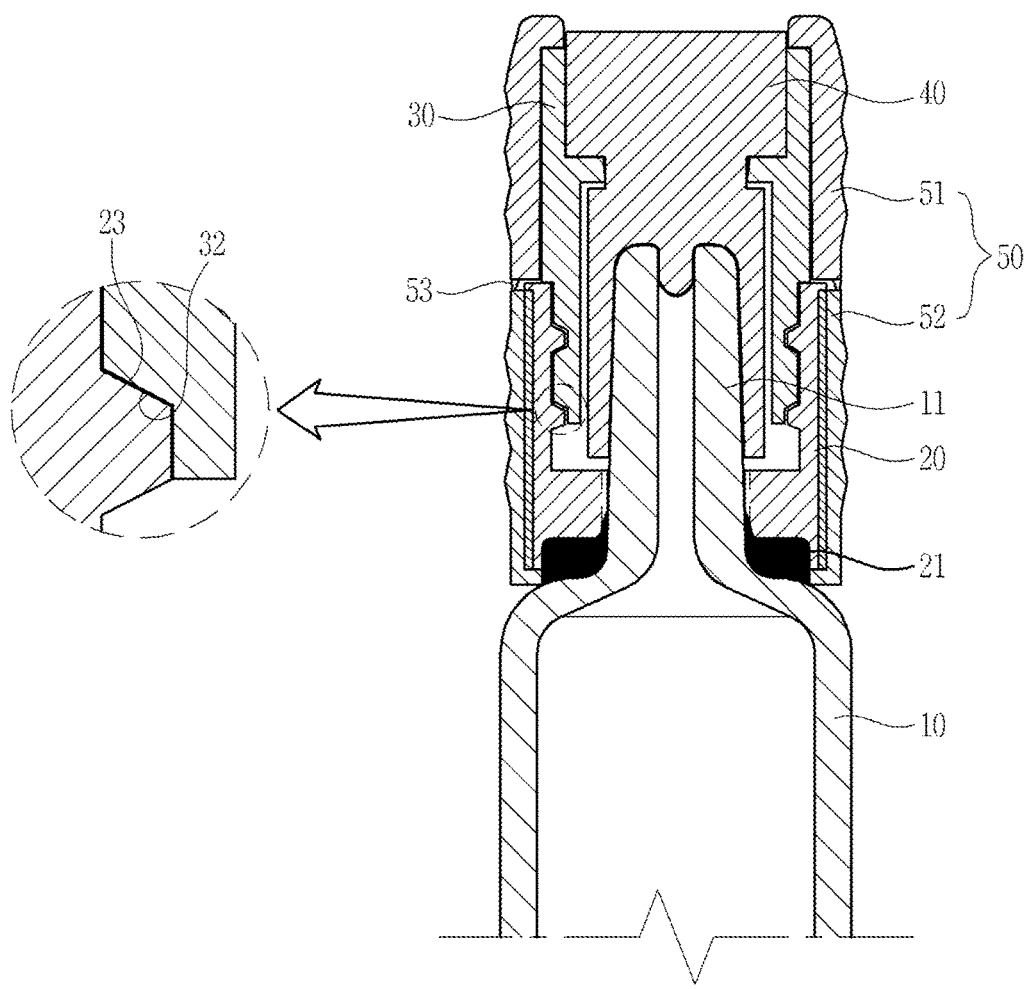
FIG. 6 is a schematic view illustrating the syringe cap having a reuse prevention structure fitted over the top of a syringe barrel.
Figure 7:
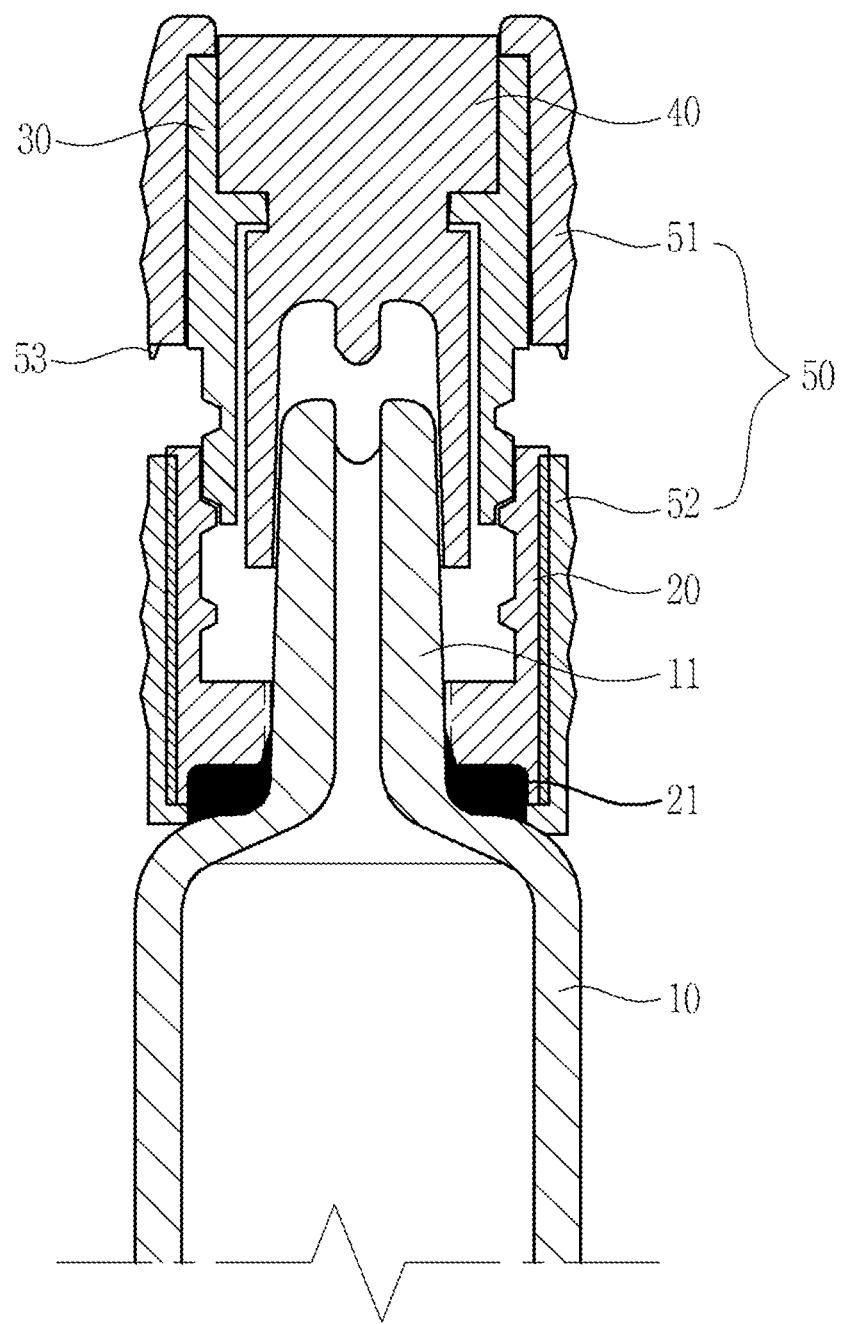
FIG. 7 is a schematic view illustrating a state where an upper body and a separable body of the syringe cap having a reuse prevention structure are being separated from each other.
Figure 8:
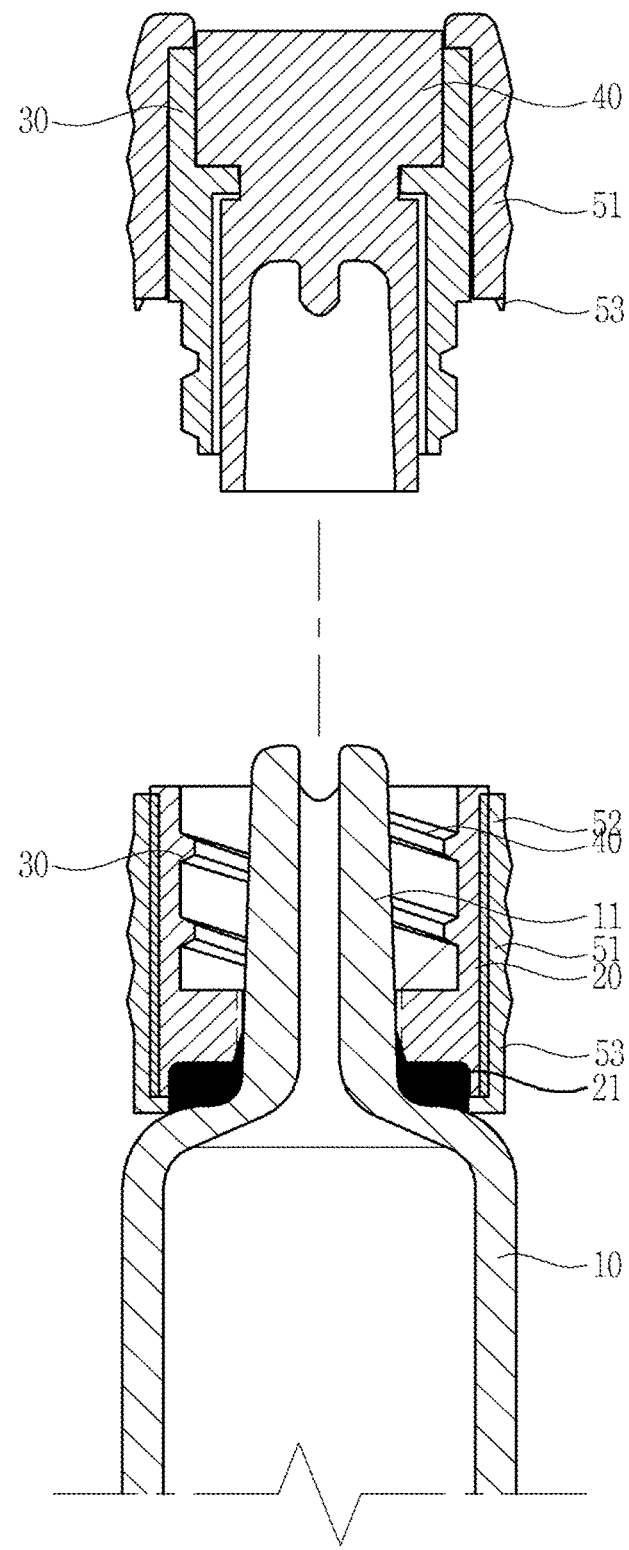
FIG. 8 is an exploded schematic view illustrating a separated state of the upper body and the separable body of the syringe cap having a reuse prevention structure.
Figure 9:
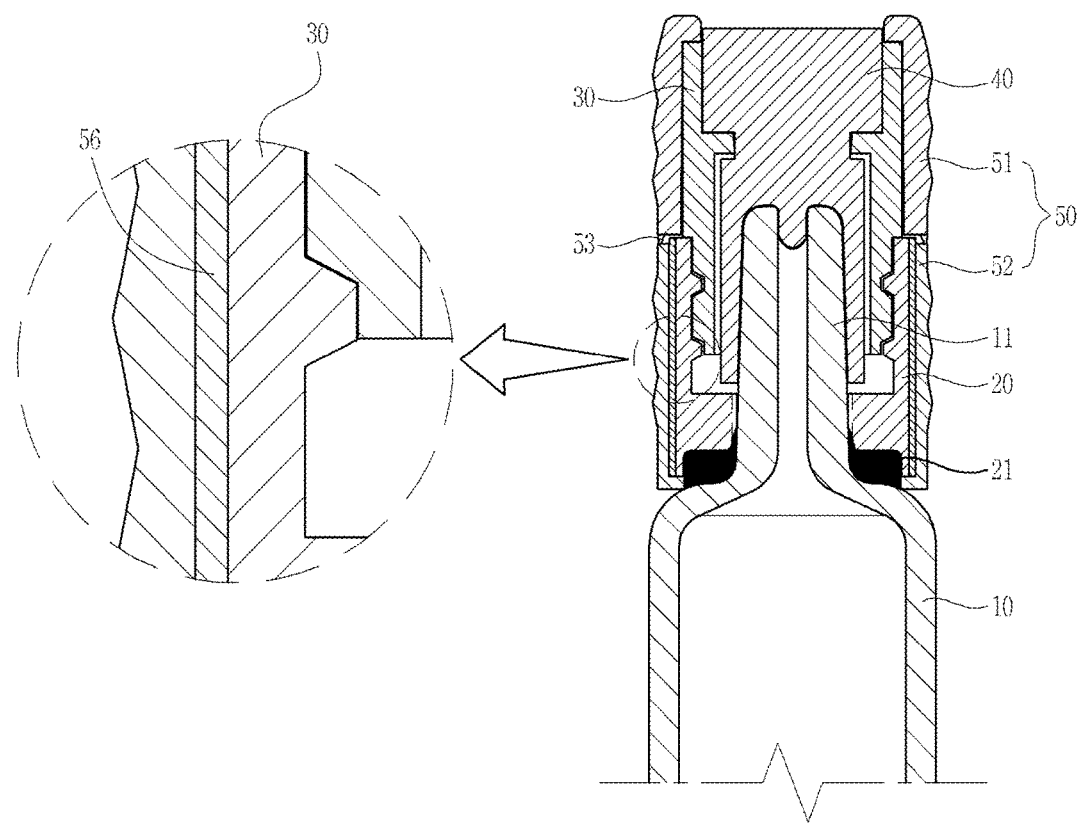
FIG. 9 is a schematic view illustrating another embodiment of the syringe cap having a reuse prevention structure.
Figure 10:
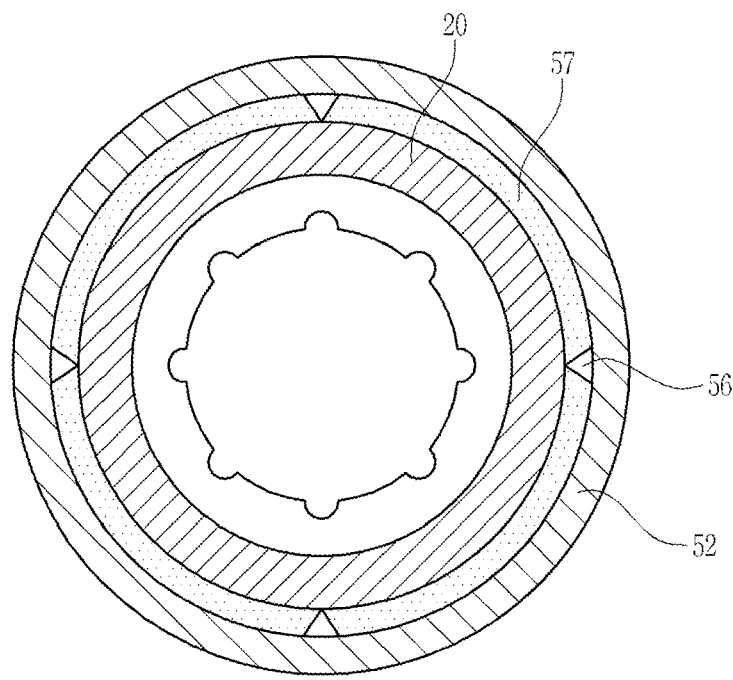
FIG. 10 is a schematic plan view illustrating another embodiment of the syringe cap having a reuse prevention structure.
Figure 11:
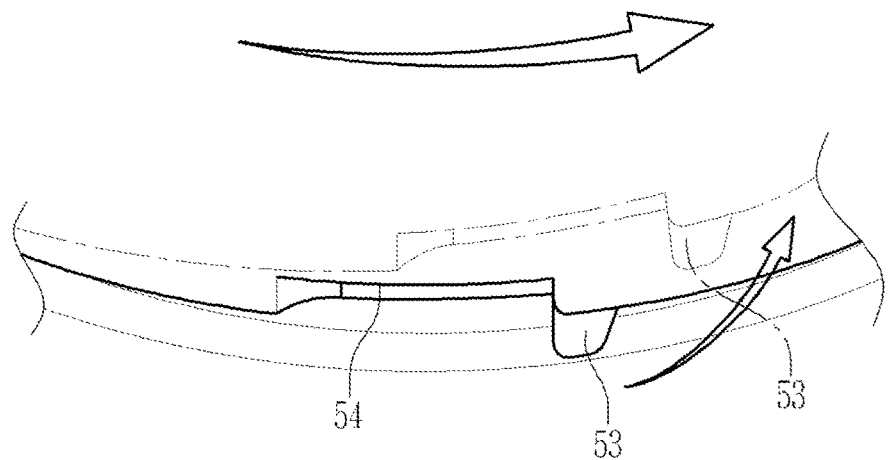
FIG. 11 is a conceptual view illustrating the separation of a connection breakable portion of the syringe cap having a reuse prevention structure.

Hereinbelow, in order to clearly disclose other purposes and features of the present invention other than the purpose, an exemplary embodiment of the present invention will be described in detail with reference to the accompanying drawings.

Unless defined differently, all terms used therein including technical and scientific terms have the same meaning generally understood by a person skilled in the art. Terms generally used and defined in a dictionary should be understood as meanings corresponding to contextual meanings of related art. In addition, unless defined clearly in the application, terms should not be understood as ideal or excessively formal meanings.

Hereinafter, a syringe cap having a reuse prevention structure according to an embodiment of the present invention will be described in detail with reference to the accompanying drawings.

As illustrated, a syringe cap having a reuse prevention structure, includes: a fixed body 20 with a spiral protrusion 22 on an inner circumferential surface thereof, into which a dispensing tip 11 of a syringe barrel 10 is fitted, and whose bottom is coupled to the syringe barrel 10 by a fusion welding portion 21; a separable body 30 with a spiral groove 31 on a lower part of an outer circumferential surface thereof, the spiral groove 31 being spirally engaged with the spiral protrusion 22 provided on the inner circumferential surface of the fixed body 20; a rubber packing 40 fitted in the separable body 30 to seal and block the dispensing tip 11 of the syringe barrel 10 coupled to the fixed body 20; and a reuse prevention cover 50 fitted over both the fixed body 20 and the separable body 30 to cover the fixed body 20 and the separable body 30.

The fixed body 20 and the separable body 30 are spirally coupled to each other by engagement of the spiral protrusion 22 of the fixed body 20 and the spiral groove 31 of the separable body 30, so the fixed body 20 and the separable body 30 can be spirally separated from each other when rotating the separable body 30 relative to the fixed body 20.

The rubber packing 40 may be made of a rubber material or a silicon material, a packing fixing groove 41 is provided on an outer circumferential surface of the rubber packing 40, and a packing fixing protrusion 30a is provided in the separable body 30. The packing fixing protrusion 30a is inserted into the packing fixing groove 41 to prevent the detachment of the rubber packing 40 from the separable body 30.

In addition, a discharge prevention protrusion 42 is provided on a lower inner side of the rubber packing 40 and is inserted into the dispensing tip 11 of the syringe barrel 10 to prevent the discharge of an injection fluid from the dispensing tip 11 before use.

As the dispensing tip 11 of the syringe barrel 10 is inserted into the rubber packing 40, the discharge of an injection fluid contained in the syringe barrel 10 is prevented by blocking the dispensing tip 11. Also, since the rubber packing 40 is fixed and coupled to the inside of the separable body 30, the rubber packing 40 is also separated when the separable body 30 is separated from the fixed body 20, thereby opening the dispensing tip 11 of the syringe barrel 10.

According to the present invention, it can be checked whether a syringe has been used by checking the reuse prevention cover 50 fitted over the outer surfaces of the fixed body 20 and the separable body 30, thereby preventing the reuse of the syringe.

The reuse prevention cover 50 includes an upper body 51 fitted over the outer surface of the separable body 30; and a lower body 52 fitted over the outer surface of the fixed body 20, and positioned below a lower part of the upper body 51, the top of the lower body 52 being spaced apart from the bottom of the upper body 51.

In addition, the upper body 51 includes a connection breakable portion 53 which integrally connects the upper body 51 and the lower body 52 by connecting the bottom of the upper body 51 to the top of the lower body 52, and is broken by rotating the upper body 51 relative to the lower body 52 in a direction to separate the bottom of the upper body 51 from the top of the lower body 52, such that the separable body 30 covered with the upper body 51 is separated from the fixed body 20 to open the fixed body 20.

Accordingly, when a user rotates the upper body 51 relative to the lower body 52 in a state of holding the upper body 51 and the lower body 52 with both hands, respectively, the connection breakable portion 53 is broken, and the upper body 51 is separated from the lower body 52. At this time, the separable body 30 covered with the upper body 51 is separated from the fixed body 20, so the dispensing tip 11 of the syringe barrel 10 is opened.

The connection breakable portion 53 is in a tapered shape that gradually narrows from the bottom of the upper body 51 to the top of the lower body 52 so as to enable easy breakage thereof by a twisting external force when rotating the upper body 51 relative to the lower body 52.

Accordingly, the connection breakable portion 53 is twisted and broken by an external force generated when rotating the upper body 51 in one direction relative to the lower body 52, thereby easily separating the upper body 51 from the lower body 52, and preventing the generation of sharp portions, i.e. burrs, on the top of the lower body 52.

Since the bottom of the fixed body 20 is coupled to the syringe barrel 10 by the fusion welding portion 21 famed on the front end of the syringe barrel 10 by fusion or welding, the fixed body 20 is stably coupled and fixed to the front end of the syringe barrel 10 when rotating the upper body 51 of the reuse prevention cover 50 relative to the lower body 52 while holding the two bodies 51 and 52 with hands. Thus, the separable body 30 is easily separated from the fixed body 20.

According to the present invention, the spiral protrusion 22 of the fixed body 20 includes a tapered first pushing slope 23, and the spiral groove 31 of the separable body 30 includes a second pushing slope 32 corresponding to the first pushing slope 23 such that when rotating the upper body 51 of the reuse prevention cover 50 in one direction relative to the lower body 52 in a state of pushing the upper body 51 toward the lower body 52, the upper body 51 is pushed up by the lower body 52, thereby being easily broken due to breaking of the connection breakable portion 53 connecting the upper body 51 and the lower body 52 to each other.

Accordingly, when rotating the upper body 51 of the reuse prevention cover 50 relative to the lower body 52, the spiral groove 31 of the separable body 30 covered with the upper body 51 is spirally rotated along the spiral protrusion 22 of the fixed body 20. At this time, as the second pushing slope 32 of the spiral groove 31 is rotated by being pushed by the first pushing slope 23 of the spiral protrusion 22, the force of pushing the second pushing slope 32 by the first pushing slope 23 is applied thereto. Thus, since the separable body 30 can easily be rotated spirally from the fixed body 20, the separable body 30 is easily separated from the separable body 30 by rotating the upper body 51 of the reuse prevention cover 50 with a predetermined force.

According to the present invention, the connection breakable portion 53 is easily broken by both the external force caused by rotation generated when rotating the upper body in one direction relative to the lower body 52, and the pushing-up motion of the separable body 30 from the fixed body 20.

Quadrangular pyramid-shaped slip prevention protrusions 59 may be provided by protruding on the upper surfaces of the upper body 51 and the lower body 52 to prevent a slip when rotating the upper body 51 in one direction relative to the lower body 52 in a state of holding the upper body 51 and the lower body 52 with hands. Accordingly, since the quadrangular pyramid-shaped slip prevention protrusions 59 protrude, a slip is prevented when rotating the upper body 51 in one direction relative to the lower body 52, thereby enabling the easy breakage of the connection breakable portion 53.

In other words, when a user rotates the upper body 51 relative to the lower body 52 by grasping the upper body 51 and the lower body 52 of the reuse prevention cover 50 with both hands, the slip of the user's both hands grasping the upper body 51 and the lower hand 52 is prevented by the quadrangular pyramid-shaped slip prevention protrusions 59. Accordingly, since a user stably grasps the upper body 51 and the lower body 52 with hands, the upper body 51 of the reuse prevention cover can be efficiently separated from the lower body 52 by breakage of the connection breakable portion 53 performed with a predetermined force, and the separable body 20 covered with the upper body 51 can easily be separated from the fixed body 30 covered with the lower body 52.

Since the separable body 30 is separated from the fixed body 20 by the breaking of the connection breakable portion 53 integrally connecting the upper body 51 and the lower body 52 of the reuse prevention cover 50 too each other, the connection breakable portion 53 is broken after the reuse prevention cover 50 is used once. Accordingly, it can be checked by naked eye whether the syringe has been used by examining whether the connection breakable portion 53 has been broken, thereby prevention the reuse of the syringe.

According to the present invention, the bottom of the upper body 51, on which the connection breakable portion 53 is provided, further includes a concave portion 54 which is connected to the connection breakable portion 53 and is concaved upward from the bottom of the upper body 51 such that the bottom of the connection breakable portion 53 is easily broken from the top of the lower body 52 by twist of the connection breakable portion 53 when rotating the upper body 51 in one direction relative to the lower body 52.

Since the concave portion 54 is connected to the connection breakable portion 53, the connection breakable portion 53 may easily be twisted by the twist of the concave portion 54 when rotating the upper body 51 of the reuse prevention cover 50 in one direction relative to the lower body 52. Thus, since the bottom of the connection breakable portion 53 is easily broken from the top of the lower body 52, the upper body 51 of the reuse prevention cover 50 can be separated from the lower body, and the separable body 20 covered with the upper body 51 can be separated from the fixed body 30 covered with the lower body 52.

In addition, a direction mark 51a showing a rotation direction of the upper body 51 is provided on the upper body 51 of the reuse prevention cover 50, and may be in the shape of an arrow pointing a direction toward the connection breakable portion 53 from the concave portion 54.

Accordingly, when rotating the upper body 51 relative to the lower body 52, a user can efficiently rotate the upper body 51 in a direction shown by the arrow-shaped direction mark 51a, so the concave portion 54 is twisted and the connection breakable portion 53 is easily broken.

According to the present invention, on an upper part of the outer circumferential surface of the upper body 51 of the reuse prevention cover 50, the upper body 51 further includes an inclined portion 55 inclined downward from the upper part of the outer circumferential surface of the upper body 51 to be easily inserted into a syringe tray insertion hole (not illustrated).

In other words, when the upper body 51 is inserted into the syringe tray insertion hole, the upper body 51 is easily inserted into the upper body 51 by the inclined portion 55 provided on an outer circumference of the upper body 51.

According to the present invention, on an inner circumferential surface of the lower body 52, which is fitted over the outer surface of the fixed body 20, of the reuse prevention cover 50, the lower body 52 further includes: a plurality of slip prevention protrusions 56 configured to come into close contact with an outer circumferential surface of the fixed body 20 to prevent a slip of the lower body 52 when rotating the upper body 52 relative to the lower body 52; and a joint portion 57 which is provided between the plurality of slip prevention protrusions 56 by using one of an adhesive, high frequency fusion, and thermal fusion to firmly joint the lower body 52 to the fixed body 20.

At this time, it is obvious that the plurality of slip prevention protrusions 56 and the joint portion 57 are provided between the lower body 52 and the separable body 30.

Since the joint portion 57 is provided between the plurality of slip prevention protrusions 56, the fixed body 20 and the lower body 52 of the reuse prevention cover 50 can stably be fixed. Accordingly, when rotating the upper body 51 of the reuse prevention cover 50 in one direction relative to the lower body 52, a user can stably grasp and support the lower body, thereby prevention a slip, separating the upper body 51 of the reuse prevention cover 50 from the lower body 52, and easily separating the separable body 20 fitted to be covered by the upper body 51 from the fixed body 30 fitted to be covered by the lower body 52.

According to the present invention, the lower body 52 further includes a plurality of radially-spaced cut portions 58 configured to be opened when the upper body 51 and the lower body 52 are fitted over the separable body 30 and the fixed body 20, and to be closed again when the lower body 52 is completely fitted over the fixed body 20, thereby allowing the upper body 51 and the lower body 52 of the reuse prevention cover 50, which are connected to each other by the connection breakable portion 53, to be easily fitted over the outer surfaces of the separable body 30 and the fixed body 20.

The reason for providing the plurality of cut portions 58 is for easy combination by easily fitting the reuse prevention cover 50 including the upper body 51 and the lower body 52, which are integrally famed by the connection breakable portion 53, on the fixed body 20 and the separable body 30 after combining the fixed body 20 with the separable body 30. In other words, when the reuse prevention cover 50 is fitted over the fixed body 20 and the separable body 30, the cut portions 58 are opened. After that, when the reuse prevention cover 50 is completely fitted over the fixed body 20 and the separable body 30 such that the upper body 51 of the reuse prevention cover 50 is positioned outside the separable body 30 and the lower body 52 of the reuse prevention cover 50 is positioned outside the fixed body 20, the cut portions 58 are returned from the opened state to the original closed state.

Although the present invention is described with reference to the exemplary embodiment, the present invention is not limited thereto, and those skilled in the art will appreciate that various modifications, additions and substitutions the present invention are possible, without departing from the scope and spirit of the present invention as disclosed in the accompanying claims.

Therefore, the idea of the present invention should not be limited to the described embodiment, and not only claims which will be described later but also all things equal or equivalent to the claims fall into the category of the idea of the present invention.

What is claimed is:

1. A syringe cap having a reuse prevention structure, the syringe cap comprising:
    a fixed body (20) with a spiral protrusion (22) on an inner circumferential surface thereof, into which a dispensing tip (11) of a syringe barrel (10) is fitted, and whose bottom is coupled to the syringe barrel (10) by a fusion welding portion (21);
    a separable body (30) with a spiral groove (31) on a lower part of an outer circumferential surface thereof, the spiral groove (31) being spirally engaged with the spiral protrusion (22) provided on the inner circumferential surface of the fixed body (20);
    a rubber packing (40) fitted in the separable body (30) to seal and block the dispensing tip (11) of the syringe barrel (10) coupled to the fixed body (20); and
    a reuse prevention cover (50) fitted over the fixed body (20) and the separable body (30) to cover the fixed body (20) and the separable body (30),
    wherein the reuse prevention cover (50) includes:
    an upper body (51) fitted over the separable body (30) to cover an outer surface of the separable body (30);
    a lower body (52) fitted over the fixed body (20) to cover an outer surface of the fixed body (20), and positioned below a lower end of the upper body (51) such that a top of the lower body (52) is spaced apart from a bottom of the upper body (51); and
    a connection breakable portion (53) which integrally connects the upper body (51) and the lower body (52) by connecting the bottom of the upper body (51) to the top of the lower body (52), and is broken by rotating the upper body (51) relative to the lower body (52) in a direction to separate the bottom of the upper body (51) from the top of the lower body (52), such that the separable body (30) covered with the upper body (51) is separated from the fixed body (20) to open the fixed body (20), and
    wherein the spiral protrusion (22) of the fixed body (20) includes a tapered first pushing slope (23), and the spiral groove (31) of the separable body (30) includes a second pushing slope (32) corresponding to the first pushing slope (23) such that when rotating the upper body (51) of the reuse prevention cover (50) in one direction relative to the lower body (52) in a state of pushing the upper body (51) toward the lower body (52), the upper body (51) is pushed up by the lower body (52), thereby being easily broken due to breaking of the connection breakable portion (53) connecting the upper body (51) and the lower body (52) to each other.

2. The syringe cap having a reuse prevention structure of claim 1, wherein the connection breakable portion (53) of the reuse prevention cover (50), which connects the bottom of the upper body (51) to the top of the lower body (52), is in a tapered shape that gradually narrows from the bottom of the upper body (51) to the top of the lower body (52), and wherein the bottom of the upper body (51), on which the connection breakable portion (53) is provided, further includes a concave portion (54) which is connected to the connection breakable portion (53) and is concaved upward from a bottom of the upper body (51) such that the bottom of the connection breakable portion (53) is easily broken from the top of the lower body (52) by twisting of the connection breakable portion (53) when rotating the upper body (51) in one direction relative to the lower body (52).

3. The syringe cap having a reuse prevention structure of claim 1, wherein on an upper part of the outer circumferential surface of the upper body (51) of the reuse prevention cover (50), the upper body (51) further includes an inclined portion (55) inclined downward from the upper part of the outer circumferential surface of the upper body (51) to be easily inserted into a syringe tray insertion hole.

4. The syringe cap having a reuse prevention structure of claim 1, wherein on an inner circumferential surface of the lower body (52), which is fitted over the outer surface of the fixed body (20), of the reuse prevention cover (50), the lower body (52) further includes: a plurality of slip prevention protrusions (56) configured to come into close contact with an outer circumferential surface of the fixed body (20) to prevent a slip of the lower body (52) when rotating the upper body (52) relative to the lower body (52); and a joint portion (57) which is provided between the plurality of slip prevention protrusions (56) by using one of an adhesive, high frequency fusion, and thermal fusion to firmly joint the lower body (52) to the fixed body (20).

5. The syringe cap having a reuse prevention structure of claim 1, wherein the lower body (52) further includes a plurality of radially-spaced cut portions (58) configured to be opened when the upper body (51) and the lower body (52) are fitted over the separable body (30) and the fixed body (20), and to be closed again when the lower body (52) is completely fitted over the fixed body (20), thereby allowing the upper body (51) and the lower body (52) of the reuse prevention cover (50), which are connected to each other by the connection breakable portion (53), to be easily fitted over the outer surfaces of the separable body (30) and the fixed body (20).

\* \* \* \* \*